(12) United States Patent
Iharada

(10) Patent No.: US 11,808,744 B2
(45) Date of Patent: Nov. 7, 2023

(54) LIQUID SAMPLE INJECTION MECHANISM FOR AN INSTRUMENT FOR ELEMENTAL ANALYSIS

(71) Applicant: SHIMADZU CORPORATION, Kyoto (JP)

(72) Inventor: Takeshi Iharada, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 180 days.

(21) Appl. No.: 17/608,690

(22) PCT Filed: Aug. 4, 2020

(86) PCT No.: PCT/JP2020/029783
§ 371 (c)(1),
(2) Date: Nov. 3, 2021

(87) PCT Pub. No.: WO2021/039305
PCT Pub. Date: Mar. 4, 2021

(65) Prior Publication Data
US 2022/0214320 A1 Jul. 7, 2022

(30) Foreign Application Priority Data
Aug. 29, 2019 (JP) .................. 2019-156869

(51) Int. Cl.
*G01N 31/12* (2006.01)
*G01N 31/10* (2006.01)
(52) U.S. Cl.
CPC ............. *G01N 31/12* (2013.01); *G01N 31/10* (2013.01)
(58) Field of Classification Search
CPC ............................... G01N 31/12; G01N 31/10
(Continued)

(56) References Cited

U.S. PATENT DOCUMENTS 3,530,292 A * 9/1970 Hill, Jr. ............. G01N 33/1846
422/78
3,840,341 A * 10/1974 Rogers ............... G01N 33/1846
436/154
(Continued)

FOREIGN PATENT DOCUMENTS

JP 59-122948 A 7/1984
JP 11160303 A * 6/1999
(Continued)

OTHER PUBLICATIONS

Office Action dated Apr. 27, 2023 in Chinese Application No. 202080042690.0.

*Primary Examiner* — Arlen Soderquist
(74) *Attorney, Agent, or Firm* — Sughrue Mion, PLLC

(57) ABSTRACT

An abnormality of a state in a system between a combustion tube and a detector can be detected without increasing device cost.
An instrument for elemental analysis includes a combustion tube (2) that has a sample injection port (3) with an open top and is for combusting a liquid sample in the inside, a sample injection mechanism (6) having a nozzle (10) and a slider (8), the nozzle (10) being for injecting a sample into the combustion tube, and the slider (8) being configured to slide between a first position and a second position above the combustion tube (2), the sample injection mechanism (6) being configured so that the sample injection port (3) of the combustion tube (2) is sealed in a state where the slider (8) is positioned at the first position, and the sample injection port (3) is unsealed and the nozzle (10) is positioned above the sample injection port (3) in a state where the slider (8) is positioned at the second position, a carrier gas supply flow path (26) communicating with the inside of the combustion tube (2) to supply carrier gas into the combustion tube (2), a pressure sensor (30) for detecting pressure in the carrier (Continued)

gas supply flow path (26), a detector (22) that detects a component in sample gas flowing out of the combustion tube (2), and an arithmetic part (44) configured to determine an abnormality degree of a state in a system between the combustion tube and the detector based on a change in pressure, which is detected by the pressure sensor (30), at the time when the slider (8) of the sample injection mechanism (6) slides from the first position to the second position.

4 Claims, 4 Drawing Sheets

(58) Field of Classification Search
USPC .......................................................... 422/80
See application file for complete search history.

(56) References Cited

U.S. PATENT DOCUMENTS

| 3,933,429 | A | * | 1/1976 | Shibata | ................ | G01N 31/005 |
| | | | | | | 436/160 |
| 4,968,485 | A | * | 11/1990 | Morita | ..................... | G01N 1/38 |
| | | | | | | 422/78 |
| 2018/0128547 | A1 | * | 5/2018 | Rawls | ................... | F16K 3/0227 |

FOREIGN PATENT DOCUMENTS

| JP | 2002031629 A | * | 1/2002 |
| JP | 2013185884 A | * | 9/2013 |

* cited by examiner

LIQUID SAMPLE INJECTION MECHANISM FOR AN INSTRUMENT FOR ELEMENTAL ANALYSIS

CROSS REFERENCE TO RELATED APPLICATIONS

This application is a National Stage of International Application No. PCT/JP2020/029783 filed Aug. 4, 2020, claiming priority based on Japanese Patent Application No. 2019-156869 filed Aug. 29, 20219.

TECHNICAL FIELD

The present invention relates to an instrument for elemental analysis.

BACKGROUND ART

A combustion oxidation type total organic carbon measuring device (TOC meter) is known (see Patent Document 1). The TOC meter heats a combustion tube in which an oxidation catalyst is arranged to a high temperature (for example, about 680° C.) by an electric furnace, and supplies carrier gas to the combustion tube at a constant flow rate. When a liquid sample is injected into the combustion tube, a carbon component contained in the sample is converted to carbon dioxide by the action of the oxidation catalyst. A detector such as an infrared carbon dioxide detector (NDIR) is connected to the combustion tube, and the carbon dioxide generated in the combustion tube is introduced to the detector together with the carrier gas so that the concentration of the carbon dioxide is measured.

PRIOR ART DOCUMENTS

Patent Documents

Patent Document 1: Japanese Patent Laid-open Publication No. 2013-185884
Patent Document 2: Japanese Patent Laid-open Publication No. 2002-031629

SUMMARY OF THE INVENTION

Problems to be Solved by the Invention

In a case where the combustion tube is cracked or broken due to aged deterioration or the like, or in a case where airtightness is not maintained due to poor connection of a pipe to the combustion tube, fluid leaks in a section between the combustion tube and the detector. For this reason, carbon dioxide generated in the combustion tube is not normally introduced to the detector. As a result, an accurate measured value cannot be obtained (for example, a measured value becomes zero or a value close to zero).

Since the combustion tube is arranged in the electric furnace, it is difficult to visually check such a failure from the outside, and when a measured value of zero or close to zero is obtained, it is difficult to determine whether the result is accurate or due to a failure of the combustion tube unless the combustion tube is taken out from the electric furnace and checked. If a fluid flow rate in a flow path connecting the combustion tube and the detector is monitored by a flow sensor, it is possible to detect an abnormality in a system between the combustion tube and the detector. However, installing such a flow sensor leads to an increase in device cost, which is not preferable.

An object of the present invention is to enable detection of an abnormality degree of a state in the system between the combustion tube and the detector without increasing device cost.

Solutions to the Problems

As a sample injection mechanism for injecting a sample into a combustion tube, there is a mechanism for sliding a slider holding a nozzle for sample injection above the combustion tube (see Patent Document 2). The sample injection mechanism is switched between a state in which a sample injection port provided on the combustion tube is sealed and a state in which the nozzle for sample injection is positioned above the sample injection port by sliding the slider.

In the state where the sample injection port of the combustion tube is sealed, as long as an abnormality of fluid leakage does not occur in the system between the combustion tube and the detector, pressure in the combustion tube is higher than the atmospheric pressure due to back pressure by an oxidation catalyst in a combustion chamber and components such as a column connected to the downstream side of the combustion tube. In this state, when the slider of the sample injection mechanism is slid to position the nozzle for sample injection above the sample injection port, the sealing of the sample injection port is temporarily released, and a temporary decrease in pressure in the combustion tube is observed. In contrast, in a case where fluid leakage occurs in the system between the combustion tube and the detector due to a failure or the like of the combustion tube, the pressure in the combustion tube becomes substantially the atmospheric pressure even in a state where the sample injection port is sealed. Accordingly, a temporary decrease in the pressure in the combustion tube due to sliding of the slider of the sample injection mechanism is hardly observed.

In the present invention, the abnormality degree in the system between the combustion tube and the detector is detected using the above phenomenon. That is, an instrument for elemental analysis according to the present invention includes a combustion tube that has a sample injection port with an open top and is for combusting a liquid sample in the inside, a sample injection mechanism having a nozzle and a slider, the nozzle being for injecting a sample into the combustion tube, and the slider being configured to slide between a first position and a second position above the combustion tube, sample injection mechanism being configured so that the sample injection port of the combustion tube is sealed in a state where the slider is positioned at the first position, and the sample injection port is unsealed and the nozzle is positioned above the sample injection port in a state where the slider is at the second position, a carrier gas supply flow path communicating with the inside of the combustion tube to supply carrier gas into the combustion tube, a pressure sensor that detects pressure in the carrier gas supply flow path, a detector for detecting components in sample gas flowing out of the combustion tube, and an arithmetic part configured to determine an abnormality degree of a state in a system between the combustion tube and the detector based on a change in pressure, which is detected by the pressure sensor, at the time when the slider of the sample injection mechanism slides from the first position to the second position.

Effects of the Invention

According to the instrument for elemental analysis of the present invention, determination on the abnormality degree of the state in the system between the combustion tube and the detector is performed based on a pressure change in the combustion tube when the slider of the sample injection mechanism slides from the first position to the second position. Therefore, the abnormality in the system between the combustion tube and the detector can be detected without increasing the device cost.

EMBODIMENTS OF THE INVENTION

Hereinafter, an embodiment of an instrument for elemental analysis according to the present invention will be described with reference to the drawings.

Figure 1:
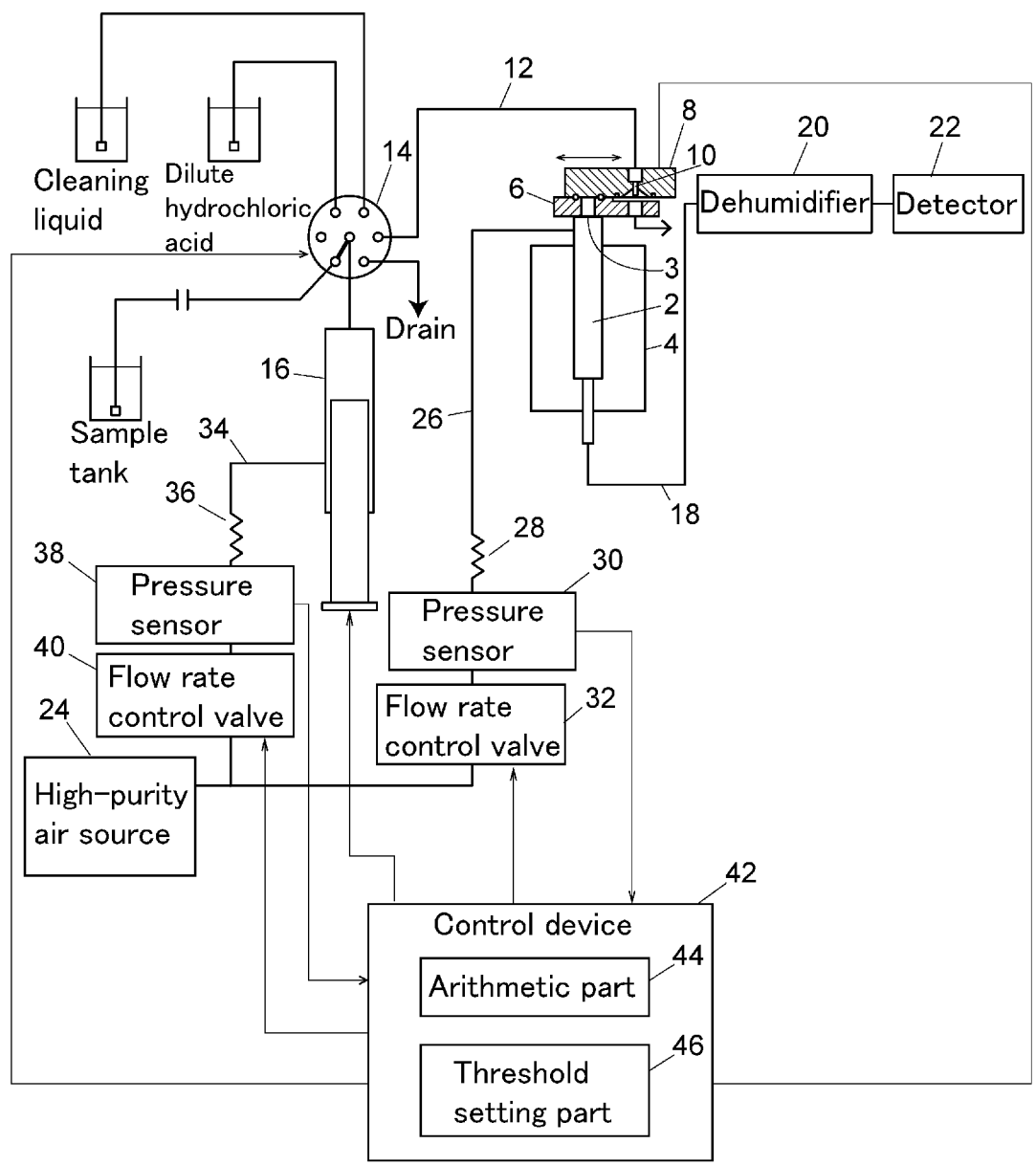
FIG. 1 is a schematic configuration diagram illustrating an embodiment of an instrument for elemental analysis.

FIG. 1 shows a schematic configuration of a combustion oxidation type TOC meter, which is one of instruments for elemental analysis.

The TOC meter of the present embodiment mainly includes a combustion tube 2, an electric furnace 4, a sample injection mechanism 6, a switching valve 14, a syringe pump 16, a Dehumidifier 20, a detector 22, and a control device 44.

The combustion tube 2 is made from, for example, quartz glass, and an oxidation catalyst is arranged inside. The combustion tube 2 is heated by the electric furnace 4 to a high temperature (for example, 680° C.) and burns a liquid sample injected to the inside to generate sample gas. The combustion tube 2 includes a sample injection port 3 with an open top.

Figure 2:
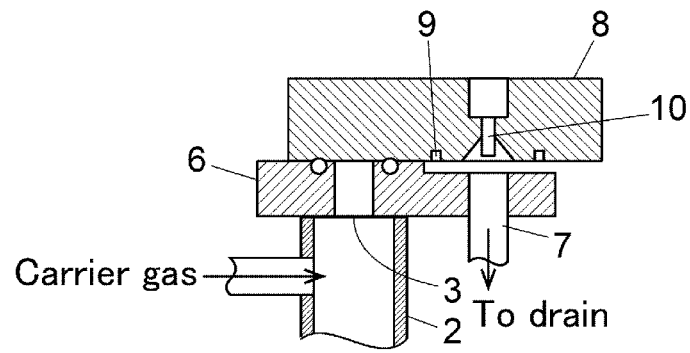
FIG. 2 is a cross-sectional view illustrating a state where a slider of a sample injection mechanism is slid to a first position.
Figure 3:
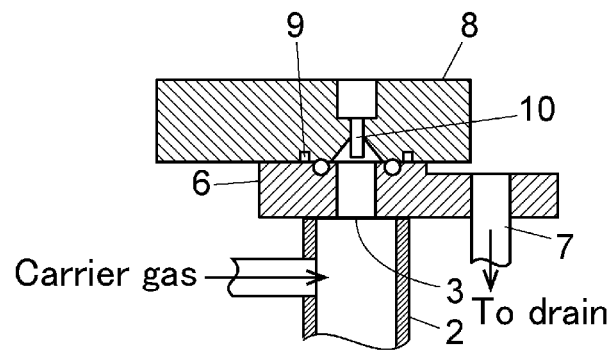
FIG. 3 is a cross-sectional view illustrating a state where a slider of a sample injection mechanism is slid to a second position.

The sample injection mechanism 6 is provided on the combustion tube 2. The sample injection mechanism 6 holds a nozzle 10 for injecting a sample into the combustion tube 2, and includes a slider 8 that slides in a horizontal direction between a first position and a second position above the combustion tube 2. When the slider 8 is at the first position, as shown in FIG. 2, the tip of the nozzle is arranged above a drain tube 7, and the sample injection port 3 of the combustion tube 2 is sealed. When the slider 8 is at the second position, as shown in FIG. 3, the tip of the nozzle 10 is arranged above the sample injection port 3 of the combustion tube 2. One end of a sample inflow flow path 12 is connected to the nozzle 10. The other end of the sample injection flow path 12 is connected to one selection port of the switching valve 14 described later.

The switching valve 14 has one central port and a plurality of selection ports. In addition to the sample injection flow path 12, a flow path leading to a sample tank, a flow path leading to a dilute hydrochloric acid container, a flow path leading to a cleaning liquid container, and a flow path leading to the drain are connected to a plurality of the selection ports of the switching valve 14. A suction/discharge port of the syringe pump 16 is connected to the central port of the switching valve 14, and a connection destination of the suction/discharge port of the syringe pump 16 can be switched by the switching valve 14. Injection of a sample into the combustion tube 2 is performed in a manner that the syringe pump 16 is connected to the sample tank, a sample in the sample tank is collected in the syringe pump 16, processing such as addition of acid to the sample or ventilation is performed as necessary in the syringe pump 16, then the slider 8 of the sample injection mechanism 6 is slid to the second position, the nozzle 10 is connected to the sample injection port 3, and the sample is discharged from the syringe pump 16.

A carrier gas supply flow path 26 is connected to the combustion tube 2. The carrier gas supply flow path 26 is a flow path for supplying high-purity air supplied from a high-purity air source 24 as carrier gas to the combustion tube 2. A resistance pipe 28, a pressure sensor 30, and a flow rate control valve 32 are provided on the carrier gas supply flow path 26. The pressure sensor 30 is for detecting pressure in the carrier gas supply flow path 26. A detection signal of the pressure sensor 30 is taken into the control device 42. The flow rate control valve 32 is for controlling a flow rate of the carrier gas flowing through the carrier gas supply flow path 26. The opening degree of the flow rate control valve 32 is controlled by the control device 42 based on an output signal of the pressure sensor 30.

An outlet of the combustion tube 2 communicates with the detector 22 via a sample gas flow path 18. The detector 22 is for measuring a carbon dioxide concentration in the sample gas generated in the combustion tube 2, and is, for example, NDIR. The Dehumidifier 20 is provided on the sample gas flow path 18, and moisture in the sample gas flowing out from the outlet of the combustion tube 2 is removed by the Dehumidifier 20.

A sparging gas supply flow path 34 is connected to a syringe of the syringe pump 16, so that sparging processing of a sample can be performed with sparging gas in the syringe of the syringe pump 16. The sparging gas supply flow path 34 is a flow path for supplying high-purity air from the high-purity air source 24 as sparging gas into the syringe of the syringe pump 16. A resistance pipe 36, a pressure sensor 38, and a flow rate control valve 40 are provided on the sparging gas supply flow path 34. The pressure sensor 38 is for detecting the pressure in the sparging gas supply flow path 34. An output signal of the pressure sensor 38 is taken into the control device 42. The flow rate control valve 40 is for controlling a flow rate of the sparging gas flowing through the sparging gas supply flow path 34. The opening degree of the flow rate control valve 40 is controlled by the control device 42 based on a detection signal of the pressure sensor 38. Note that the sparging gas supply flow path 34 does not need to be provided.

The control device 24 is for controlling the operation of the sample injection mechanism 6, the switching valve 14, the syringe pump 16, the flow rate control valve 42, and the flow rate control valve 40. The control device 42 can be realized by, for example, an electronic circuit including an arithmetic element such as a central processing unit (CPU) and a storage device.

The control device 42 includes an arithmetic part 44 and a threshold setting part 46. The arithmetic part 44 and the threshold setting part 46 are functions obtained by the CPU executing a program in an electronic circuit that realizes the control device 42.

The arithmetic part 44 is configured to execute determination on an abnormality degree of a state in a system between the combustion tube 2 and the detector 22. The determination on the abnormality degree of the state is performed based on a fluctuation of detected pressure of the pressure sensor 30 at the time when the slider 8 of the sample injection mechanism 6 is moved from the first position (see FIG. 2) to the second position (see FIG. 3). In the present embodiment, whether or not the state in the system between the combustion tube 2 and the detector 22 is normal is determined based on the presence or absence of a pressure fluctuation when the slider 8 of the sample injection mechanism 6 is moved from the first position to the second position. However, the present invention is not limited to such a mode, and the configuration may be such that the degree of a pressure fluctuation when the slider 8 of the sample injection mechanism 6 is moved from the first position to the second position is determined, and the abnormality degree (for example, normal, abnormal level 1, abnormal level 2, and the like) of the state in the system between the combustion tube 2 and the detector 22 is determined based on the degree of the pressure fluctuation.

Figure 5:
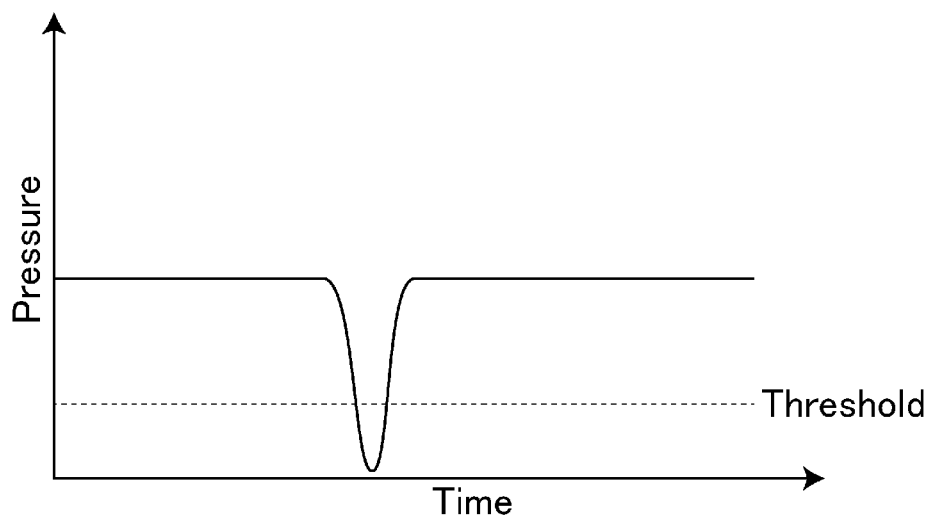
FIG. 5 is a graph showing an example of a fluctuation in pressure in a combustion tube at the time of state determination in the embodiment.

As shown in FIGS. 2 and 3, a lower surface of the slider 8 of the sample injection mechanism 6 is provided with a groove 9 that reaches an upper portion of the sample injection port 3 before the nozzle 10 when the slider 8 slides from the first position to the second position and allows the inside and the outside of the combustion tube 2 to communicate with each other. Since carrier gas is supplied at a constant flow rate into the combustion tube 2, the pressure in the combustion tube 2 is maintained substantially constant at a pressure higher than the atmospheric pressure when the slider 8 is at the first position. In this state, when the slider 8 of the sample injection mechanism 6 is slid toward the second position, and the groove 9 of the slider 8 reaches the sample injection port 3, fluid in the combustion tube 2 is discharged to the outside through the groove 9, and, as shown in FIG. 5, the pressure in the combustion tube 2 temporarily decreases substantially to the atmospheric pressure. In contrast, in a case where there is fluid leakage in the system between the combustion tube 2 and the detector 22, the pressure in the combustion tube 2 hardly increases even if the carrier gas is supplied at a constant flow rate into the combustion tube 2. For this reason, even when the slider 8 of the sample injection mechanism 6 moves from the first position to the second position, almost no fluctuation is observed in the pressure in the combustion tube 2.

Using the above phenomenon, the arithmetic part 44 determines whether or not a temporary pressure fluctuation in the combustion tube 2 as shown in FIG. 5 is detected while the slider 8 moves from the first position to the second position. Whether a pressure fluctuation occurs can be determined by whether the pressure detected by the pressure sensor 30 falls below a predetermined threshold.

The arithmetic part 44 may be configured execute the determination operation at the timing a flow rate of the carrier gas supplied to the combustion tube 2 is stabilized before the TOC meter is started and the sample injection into the combustion tube 2 is executed. Further, the arithmetic part 44 may be configured to execute the determination operation when an instruction to execute the determination operation is input by the user.

The threshold setting part 46 is configured to set a threshold used by the arithmetic part 44 for determination. The threshold can be set based on, for example, the pressure detected by the pressure sensor 30 immediately before the determination operation is executed. For example, a value lower by a certain percentage than the pressure detected by the pressure sensor 30 immediately before the determination operation is executed (where the atmospheric pressure is set to zero) can be set as the threshold.

Figure 4:
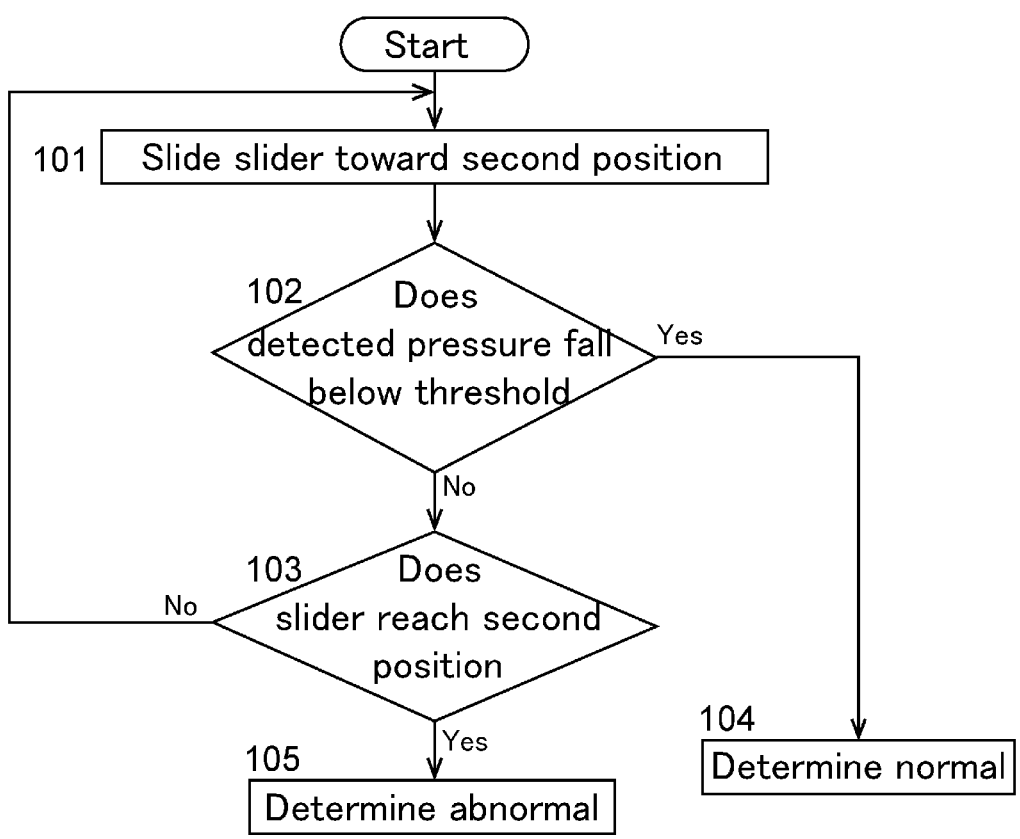
FIG. 4 is a flowchart showing an example of operation of state determination in the embodiment.

The determination operation for a state by the arithmetic part 44 will be described with reference to a flowchart of FIG. 4.

When the determination operation is started, the arithmetic part 44 slides the slider 8 of the sample injection mechanism 6 from the first position toward the second position (Step 101). The arithmetic part 44 constantly compares, with the threshold, a detected pressure of the pressure sensor 30 read by the control device 42 while the slider 8 is slid from the first position to the second position, and determines whether the detected pressure falls below the threshold (Step 102). If the detected pressure falls below the threshold before the slider 8 reaches the second position, it is determined to be normal (Steps 103 and 104), and if the detected pressure does not fall below the threshold before the slider 8 reaches the second position, it is determined to be abnormal (Steps 103 and 105).

Note that the above embodiment merely shows an example of an embodiment of the instrument for elemental analysis according to the present invention. The embodiment of the instrument for elemental analysis according to the present invention is as described below.

The embodiment of the instrument for elemental analysis according to the present invention includes a combustion tube that has a sample injection port with an open top and is for combusting a liquid sample in the inside, a sample injection mechanism having a nozzle and a slider, the nozzle being for injecting a sample into the combustion tube, and the slider being configured to slide between a first position and a second position above the combustion tube, sample injection mechanism being configured so that the sample injection port of the combustion tube is sealed in a state where the slider is positioned at the first position, and the sample injection port is unsealed and the nozzle is positioned above the sample injection port in a state where the slider is at the second position, a carrier gas supply flow path communicating with the inside of the combustion tube to supply carrier gas into the combustion tube, a pressure sensor that detects pressure in the carrier gas supply flow path, a detector for detecting components in sample gas flowing out of the combustion tube, and an arithmetic part configured to determine an abnormality degree of a state in a system between the combustion tube and the detector based on a change in pressure, which is detected by the pressure sensor, at the time when the slider of the sample injection mechanism slides from the first position to the second position.

A first aspect of the embodiment of the instrument for elemental analysis according to the present invention further includes a threshold setting part configured to set a threshold for the determination based on pressure immediately before the slider starts sliding from the first position to the second position. The arithmetic part is configured to determine normal when pressure detected by the pressure sensor falls below the threshold set by the threshold setting part during a period in which the slider slides from the first position to the second position. According to such an aspect, it is possible to easily determine the presence or absence of a pressure fluctuation in the combustion tube.

In a second aspect of the embodiment of the instrument for elemental analysis according to the present invention, the arithmetic part is configured to execute the determination by sliding the slider from the first position to the second position after the instrument for elemental analysis is started and before sample injection into the combustion tube is executed. According to such an aspect, when the instrument for elemental analysis is started, determination as to whether or not there is an abnormality in the combustion tube or the like is performed automatically. Accordingly, it is possible to prevent analysis from being started in a state where there is an abnormality in the combustion tube or the like. This second aspect can be combined with the first aspect.

In a third aspect of the embodiment of the instrument for elemental analysis according to the present invention, the arithmetic part is configured to execute the determination by sliding the slider from the first position to the second position at the time when an instruction to execute the determination is input by the user. According to such an aspect, determination as to whether or not there is an abnormality in the combustion tube or the like can be performed at a timing desired by the user.

DESCRIPTION OF REFERENCE SIGNS

2: Combustion tube
3: Sample injection port
4: Electric furnace
6: Sample injection mechanism
8: Slider
10: Nozzle
12: Sample injection flow path
14: Switching valve
16: Syringe pump
18: Sample gas flow path
20: Dehumidifier
22: Detector
24: High-purity air source
26: Carrier gas supply flow path
28, 36: Resistance pipe
30, 38: Pressure sensor
32, 40: Flow rate control valve
34: Sparging gas supply flow path
42: Control device
44: Arithmetic part
46: Threshold setting part

The invention claimed is:

1. An instrument for elemental analysis comprising:
a combustion tube that has a sample injection port with an open top and is for combusting a liquid sample therein;
a sample injection mechanism having a nozzle and a slider, the nozzle being for injecting a sample into the combustion tube, the slider being configured to slide between a first position and a second position above the combustion tube, the sample injection mechanism being configured so that the sample injection port of the combustion tube is sealed in a state where the slider is positioned at the first position, and the sample injection port is unsealed and the nozzle is positioned above the sample injection port in a state where the slider is positioned at the second position;
a carrier gas supply flow path communicating with inside of the combustion tube to supply carrier gas into the combustion tube;
a pressure sensor that detects pressure in the carrier gas supply flow path;
a detector for detecting components in sample gas flowing out of the combustion tube; and
an arithmetic part configured to determine an abnormality degree of a state in a system between the combustion tube and the detector based on a change in pressure, which is detected by the pressure sensor, at the time when the slider of the sample injection mechanism slides from the first position to the second position.

2. The instrument for elemental analysis according to claim 1, further comprising a threshold setting part configured to set a threshold for the determination based on pressure immediately before the slider starts sliding from the first position to the second position, wherein
the arithmetic part is configured to determine normal when pressure detected by the pressure sensor falls below the threshold set by the threshold setting part during a period in which the slider slides from the first position to the second position.

3. The instrument for elemental analysis according to claim 1, wherein
the arithmetic part is configured to execute the determination by sliding the sliding from the first position to the second position after the instrument for elemental analysis is started and before sample injection into the combustion tube is executed.

4. The instrument for elemental analysis according to claim 1, wherein
the arithmetic part is configured to execute the determination by sliding the slider from the first position to the second position at the time when an instruction to execute the determination is input by a user.

* * * * *